(12) United States Patent
An et al.

(10) Patent No.: US 11,746,327 B2
(45) Date of Patent: Sep. 5, 2023

(54) COMPOSITION FOR CULTURING NK CELLS AND METHOD FOR CULTURING NK CELLS USING SAME

(71) Applicant: SUNGKWANG MEDICAL FOUNDATION, Seoul (KR)

(72) Inventors: Hee Jung An, Seoul (KR); Yeon Ho Choi, Seoul (KR); Eun Jin Lim, Seongnam-si (KR); Yong Wha Moon, Seongnam-si (KR); Se Wha Kim, Seongnam-si (KR)

(73) Assignee: SUNGKWANG MEDICAL FOUNDATION, Seoul (KR)

( * ) Notice: Subject to any disclaimer, the term of this patent is extended or adjusted under 35 U.S.C. 154(b) by 228 days.

(21) Appl. No.: 16/645,215

(22) PCT Filed: Nov. 20, 2018

(86) PCT No.: PCT/KR2018/014294
§ 371 (c)(1),
(2) Date: Mar. 6, 2020

(87) PCT Pub. No.: WO2019/103436
PCT Pub. Date: May 31, 2019

(65) Prior Publication Data
US 2021/0095249 A1 Apr. 1, 2021

(30) Foreign Application Priority Data

Nov. 24, 2017 (KR) ........................ 10-2017-0158577

(51) Int. Cl.
*C12N 5/0783* (2010.01)
*A61P 35/00* (2006.01)
*A61K 35/17* (2015.01)

(52) U.S. Cl.
CPC ............ *C12N 5/0646* (2013.01); *A61K 35/17* (2013.01); *A61P 35/00* (2018.01)

(58) Field of Classification Search
CPC combination set(s) only.
See application file for complete search history.

(56) References Cited

U.S. PATENT DOCUMENTS

| 7,445,779 | B2 | 11/2008 | De Waal Malefyt et al. |
| 8,877,182 | B2 | 11/2014 | Alici |
| 9,834,753 | B2 | 12/2017 | Min et al. |
| 2011/0086004 | A1 | 4/2011 | Kindsvogel et al. |
| 2012/0258085 | A1 | 10/2012 | Alici |
| 2015/0118207 | A1 | 4/2015 | Min et al. |
| 2018/0015123 | A1 | 1/2018 | Choi et al. |

FOREIGN PATENT DOCUMENTS

| JP | 2006-514057 A | 4/2006 |
| JP | 2007-538108 A | 12/2007 |
| JP | 2017-12010 A | 1/2017 |
| KR | 1999-0042747 A | 6/1999 |
| KR | 10-2011-0132618 A | 12/2011 |
| KR | 10-2014-0123503 A | 10/2014 |
| KR | 10-2017-0000798 A | 1/2017 |
| KR | 10-2017-0010865 A | 2/2017 |
| WO | WO 2016/209021 A1 | 12/2016 |
| WO | WO-2016209021 A * | 12/2016 ............ A61K 35/17 |

OTHER PUBLICATIONS

Rubnitz, "NKAML: A Pilot Study to Determine the Safety and Feasibility of Haploidentical Natural Killer Cell Transplantation in Childhood Acute Myeloid Leukemia," J Clin Oncol 28:955-959. (Year: 2010).*
Curti et al., "Successful transfer of alloreactive haploidentical KIR ligand-mismatched natural killer cells after infusion in elderly high risk acute myeloid leukemia patients," Blood. 2011;118(12):3273-3279. (Year: 2011).*
Cantoni et al., "Role of NK cells in immunotherapy and virotherapy of solid tumors," Immunotherapy 7(8), pp. 861-882. (Year: 2015).*
WO/2016209021 Baek et al., Method for Proliferating Natural Killer Cells, Machine Translation to English Wipo Translate [retrieved on Mar. 23, 2022]. Retrieved from the internet: <URL: https://patentscope.wipo.int/search/en/detail.jsf?docId=WO2016209021&_cid=P11-L14G48-30248-1> (Year: 2016).*
McInnes et al., "Cytokines in the pathogenesis of rheumatoid arthritis," Nature Reviews Immunology 7.6 pp. 429-442 (Year: 1997).*
WO/2016209021 Cha et al., Method for Proliferating Natural Killer Cells, Machine Translation to English Wipo Translate [retrieved on Mar. 23, 2022], Retrieved from the internet: <URL: https://patentscope.wipo.int/search/en/detail.jsf?docId=WO2016209021&_cid=P11-L14G48-30248-1> (Year: 2016).*
Becker et al., "Selection and expansion of natural killer cells for NK cell-based immunotherapy," Cancer Immunol Immunother 65 pp. 477-484 (Year: 2016).*
Nahleh et al., "How to reduce your cancer risk: mechanisms and myths," International Journal of General Medicine 4 pp. 277-287 (Year: 2011).*

(Continued)

*Primary Examiner* — Daniel C Gamett

(74) *Attorney, Agent, or Firm* — Oblon, McClelland, Maier & Neustadt, L.L.P.

(57) ABSTRACT

Provided are a composition for culturing NK cells, and a method of culturing NK cells using the same. According to an aspect, in culturing NK cells from peripheral blood mononuclear cells, when NK cells are cultured in a medium including the composition for culturing NK cells, the composition including IL-15, IL-18, and IL-27, the NK cells may proliferate in large quantities and activation of NK cells may be promoted. Therefore, when the NK cells are used, cancer cell apoptosis or cancer cell-killing ability may be promoted. Accordingly, the NK cells may be used as an effective adoptive immune cell therapy product in cancer prevention or treatment.

2 Claims, 17 Drawing Sheets

(56) References Cited

OTHER PUBLICATIONS

Lee et al., "The effects of various hormones and growth factors on the growth of human insulin-producing cell line in serum-free medium," Experimental and Molecular Medicine, vol. 29, No. 4, pp. 209-216. (Year: 1997).*

Ziblat et al., "IL-27 stimulates human NK-cell effector functions and primes NK cells for IL-18 responsiveness," Eur. J. Immunol. 45: pp. 192-202. (Year: 2015).*

Suck et al., "Interleukin-15 supports generation of highly potent clinical-grade natural killer cells in long-term cultures for targeting hematological malignancies," Experimental Hematology39:904-914. (Year: 2011).*

Yang et al., "Phase I Study of Random Healthy Donor-Derived Allogeneic Natural Killer Cell Therapy in Patients with Malignant Lymphoma or Advanced Solid Tumors," Cancer Immunol Res; 4(3) Mar. 2016 pp. 215-224, Supplemental 1-5. (Year: 2016).*

Michaud et al., J Immunother. May 2010;33(4):382-390 (Year: 2010).*

Roda et al., J Immunol. Jul. 1, 2006;177(1):120-129 (Year: 2006).*

International Search Report dated May 24, 2019 in PCT/KR2018/014294 filed on Nov. 20, 2018, citing documents AA-AE and AN-AS therein, 3 pages.

Carrega, P. et al., "Natural Killer Cells Infiltrating Human Nonsmall-Cell Lung Cancer Are Enriched in CD56$^{Bright}$CD16$^-$ Cells and Display an Impaired Capability to Kill Tumor Cells," Cancer, vol. 112, No. 4, Feb. 2008, pp. 863-875.

Jinushi, M. et al., "Impairment of natural killer cell and dendritic cell functions by the soluble form of MHC class I-related chain A in advanced human hepatocellular carcinomas," Journal of Hepatology, vol. 43, 2005, pp. 1013-1020.

Bauernhofer, T. et al., "Preferential apoptosis of CD56$^{dim}$ natural killer cell subset in patients with cancer," Eur. J. Immunol., vol. 33, 2003, pp. 119-124.

Mocchegiani, E. et al., "Role of zinc and $\alpha_2$ macroglobulin on thymic endocrine activity and on peripheral immune efficiency (natural killer activity and interleukin 2) in cervical carcinoma," British Journal of Cancer, vol. 79, No. 2, 1999, pp. 244-250.

Tajima, F. et al., "Natural killer cell activity and cytokine production as prognostic factors in adult acute leukemia," Leukemia, vol. 10, No. 3, Mar. 1996, pp. 478-482, 2 total pages (only English Abstract).

Japanese Office Action dated May 11, 2021 in Japanese Patent Application No. 2020-513912 (with English translation), citing documents AO through AQ, AX and AY therein, 11 pages.

Martinez, A.P., et al., "Clinical grade activated natural killer products for adoptive immunotherapy against high-risk malignancies", Haematologica, vol. 100 Suppl. 1 (2015) pp. 289-290.

Frias, A.M., et al., "Generation of functional natural killer and dendritic cells in a human stromal-based serum-free culture system designed for cord blood expansion", Experimental Hematology, vol. 36, (2008) pp. 61-68.

Korean Office Action dated Feb. 18, 2021 in Korean Patent Application No. 10-2017-0158577 (with translation), citing documents AX and AY therein, 8 pages.

Norberto Walter Zwirner, et al., "Regulation of NK Cell Activation and Effector Functions by the IL-12 Family of Cytokines: The Case of IL-27" Frontiers in Immunology, vol. 8, Article 25, Jan. 2017, pp. 1-7.

Sunwoong S. Choi, et al., "Interleukin-15 Enhances Cytotoxicity, Receptor Expression, and Expansion of Neonatal Natural Killer Cells in Long-Term Culture" Clinical and Diagnostic Laboratory Immunology, vol. 11, No. 5, Sep. 2004, pp. 879-888.

\* cited by examiner

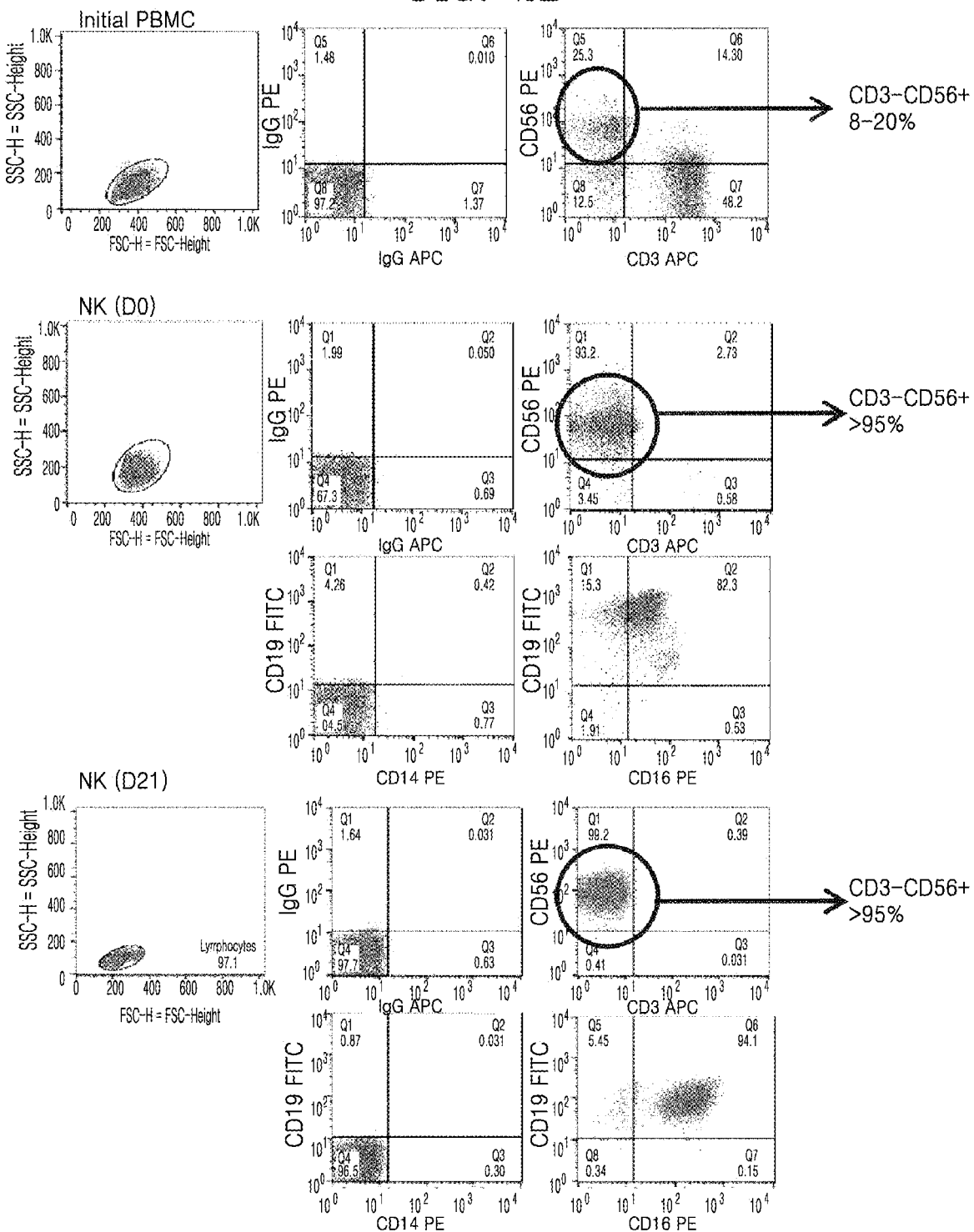

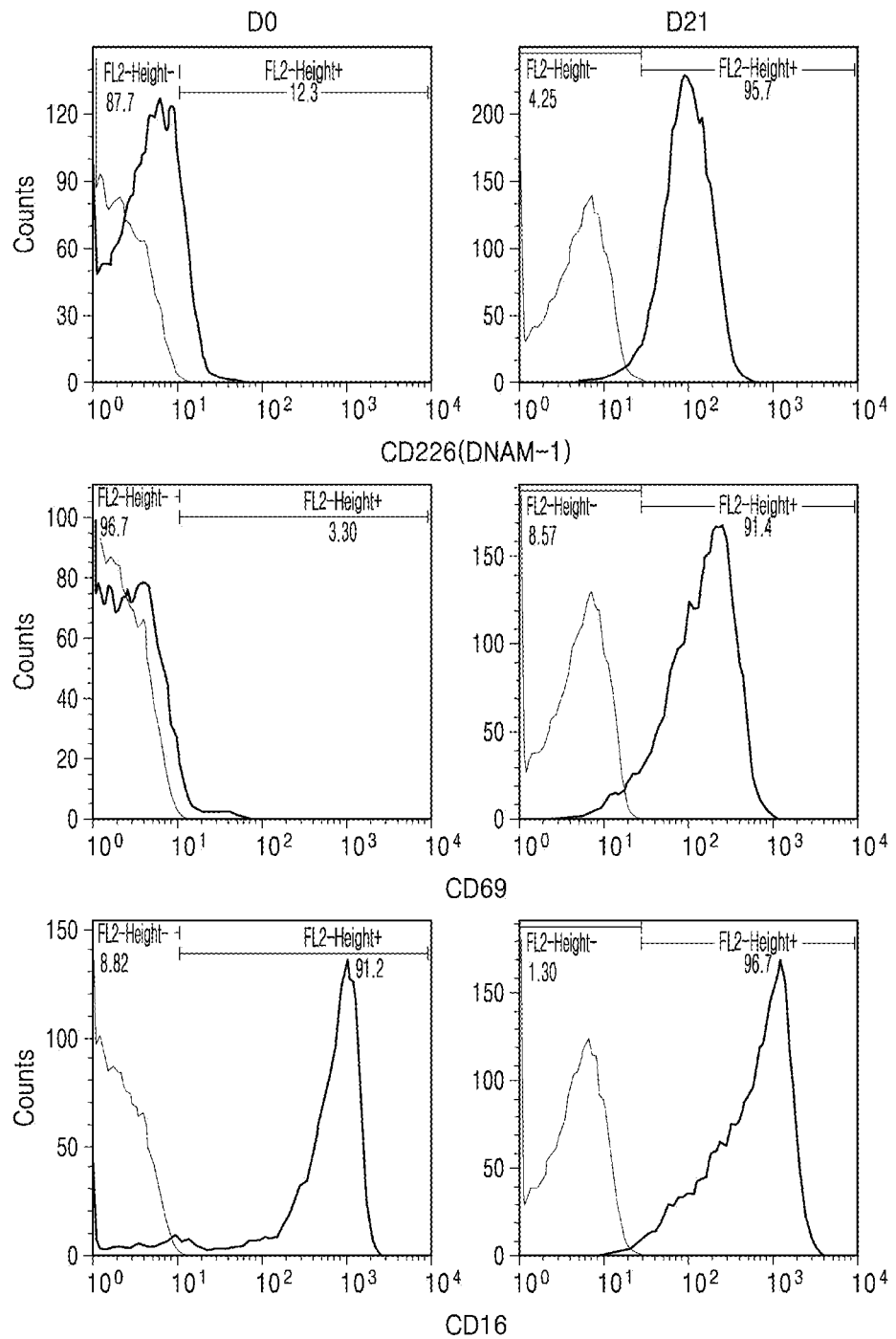

FIG. 5B
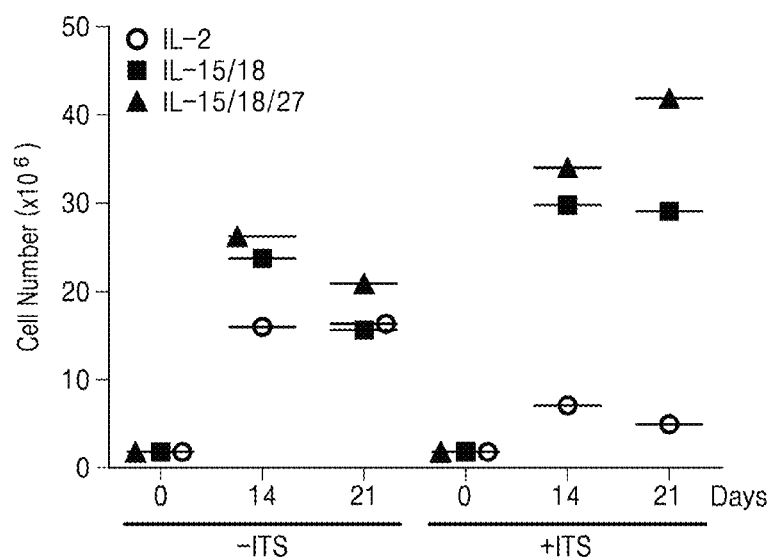
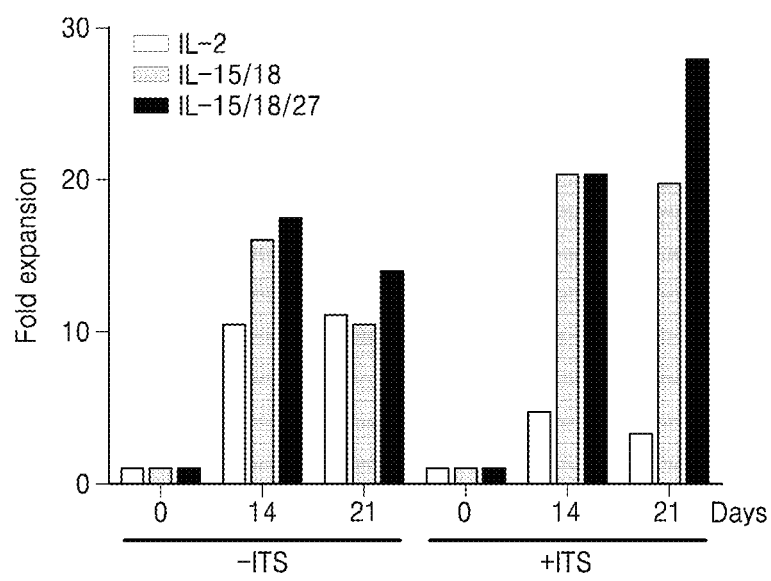

FIG. 6B
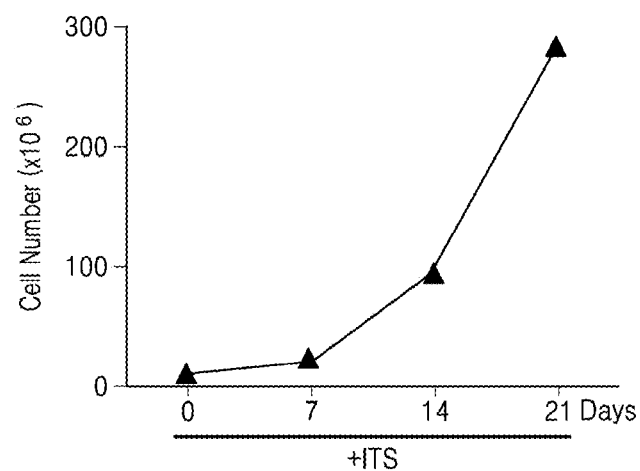
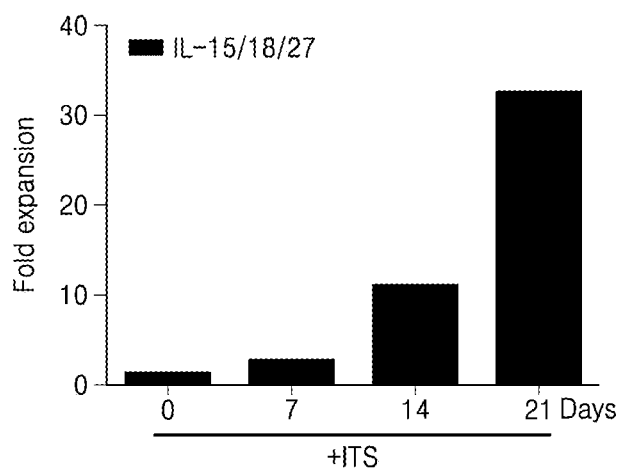

COMPOSITION FOR CULTURING NK CELLS AND METHOD FOR CULTURING NK CELLS USING SAME

TECHNICAL FIELD

This application claims priority benefits from Korean Patent Application No. 10-2017-0158577, filed on Nov. 24, 2017, the entire content of which is fully incorporated herein by reference.

The present disclosure relates to a composition for culturing natural killer (NK) cells and a method of culturing NK cells using the same.

BACKGROUND ART

Current cancer therapies generally include surgery, radiation therapy, chemotherapy, etc., which are used alone or in combination depending on the type and stage of cancer. However, these therapies are accompanied by significant adverse side effects and pain in patients. The best cancer therapy is a method of selectively killing only cancer cells without damaging normal cells. However, the existing therapies cause some damage to normal cells. Recently emerging cancer immunotherapy is a therapy that more specifically removes cancer cells while minimizing damage to normal cells by utilizing the body's own immune system. Various sub-fields (antibody therapy, immune cell therapy, viral immunotherapy, nanotechnology for immunotherapy, etc.) have been actively studied. Among them, immune cell therapy is a method of treating cancer by increasing the number of natural killer (NK) cells, natural killer T cells, T cells, B cells, dendritic cells, etc. in lymphocytes obtained from a patient's blood, enhancing their function in vitro, and then returning them to the body. Such therapies using immune cells exhibit good effects in immune response-modulating treatment, and are considered to be excellent in terms of toxicity and safety. Among the immune cells, NK cells are important cells responsible for innate immunity. Unlike T cells, NK cells mature in liver and bone marrow. In particular, NK cells have functions of identifying and killing abnormal cells such as virus-infected cells or tumor cells. Over the last decade, tumor immunotherapy using patients' immune systems has been steadily developed, and 'cell therapy products' using the same have been commercialized. Cell therapy products are defined as medical products used for treatment, diagnosis, or prevention through a series of actions that change biological characteristics of cells using a method of propagating and selecting autologous, allogeneic, or xenogeneic cells in vitro (Korea Food & Drug Administration Notification No. 2003-26 Article 2).

There is a need for a method of proliferating NK cells in large quantities and a method of culturing NK cells with enhanced activity, which are capable of solving the problem of immune rejection and providing personalized cell therapy as cell therapy for treating intractable diseases such as cancer.

DESCRIPTION OF EMBODIMENTS

Technical Problem

An aspect provides a composition for culturing natural killer (NK) cells.

Another aspect provides a method of culturing NK cells using the composition for culturing NK cells.

Solution to Problem

An aspect provides a composition for culturing natural killer (NK) cells, the composition including IL-15, IL-18, IL-27, or a combination thereof.

The composition for culturing NK cells may further include insulin-transferrin-selenium (ITS).

NK cells are large granular lymphocytes (LGL) which is a type of lymphocytes. They have excellent ability to kill infected virus and tumor cells, and have a characteristic of not killing most normal cells. Thus, NK cells play an important role in the early stages of viral infection or tumorigenesis before large quantities of active cytotoxic T lymphocytes are produced. For example, when NK cells are in contact with target cells, some molecules lyse the cells by creating pores in the membrane of the target cells while other molecules enter the target cells and increase fragmentation of nuclear DNA, leading to necrosis, apoptosis, or programmed cell death.

As a result, NK cells are able to lyse specific virus-infected cells and cancer cells in the absence of prior stimulation. Unlike cytotoxic T lymphocytes which recognize specific antigens through TCR expression, NK cells lack antigen-specific receptors. NK cells express a killer cell immunoglobulin-like receptor (KIR) that binds with MHC class I of normal cells. Binding of KIR with MHC class I produces intracellular signaling that induces inhibition of specific transcription factors. As a result, NK cell activation, and target cell lysis and disruption are inhibited. Virus-infected cells or cancer cells have significantly reduced numbers of MHC class I molecules on their surfaces. Thus, when such cells encounter NK cells, they fail to effectively engage KIRs and therefore are exposed to NK cell-mediated cytotoxicity and finally lysed.

The NK cells may be derived from, for example, a mammal, a human, a monkey, a pig, a horse, a cow, a sheep, a dog, a cat, a mouse, a rabbit, etc. The NK cells may be obtained from a normal person or a cancer patient. The NK cells may be isolated from blood or peripheral blood mononuclear cells (PBMCs). A method of isolating blood, a method of isolating PBMCs therefrom, or a method of isolating NK cells therefrom may be performed by a known method.

The composition may include IL-15, IL-18, IL-27, or a combination thereof, in which IL-15 may directly promote growth and differentiation of NK cells through IL-15 receptor expressed in NK cells, IL-18 may induce interferon gamma production of NK cells and may enhance cytotoxicity, and IL-27 may regulate the immune response, may enhance a survival rate of NK cells, and may enhance expression of interferon gamma.

The composition may further include ITS, in which ITS may improve NK cell proliferative capacity of the composition for culturing NK cells, the composition including IL-15, IL-18, IL-27, or a combination thereof.

In an NK cell culture medium, a concentration of IL-15 may be about 0.1 ng/ml to about 1000 ng/ml, about 0.2 ng/ml to about 500 ng/ml, about 0.5 ng/ml to about 200 ng/ml, about 1.0 ng/ml to about 100 ng/ml, about 2.0 ng/ml to about 50 ng/ml, or about 5.0 ng/ml to about 20 ng/ml, a concentration of IL-18 may be about 0.25 ng/ml to about 2500 ng/ml, about 0.5 ng/ml to about 1250 ng/ml, about 1.25 ng/ml to about 500 ng/ml, about 2.5 ng/ml to about 250 ng/ml, about 5.0 ng/ml to about 125 ng/ml, about 12.5 ng/ml to about 50 ng/ml, and a concentration of IL-27 may be about 0.20 ng/ml to about 2000 ng/ml, about 0.40 ng/ml to about 1000 ng/ml, about 1.0 ng/ml to about 400 ng/ml, about 2.0 ng/ml to about 200 ng/ml, about 4.0 ng/ml to about 100 ng/ml, about 10.0 ng/ml to about 40 ng/ml.

The composition may further include IL-7, IL-21, or a combination thereof. IL-21 may induce maturation of NK cell precursors from bone marrow, and in particular, may increase effector functions such as cytokine production capacity and cell killing capacity of NK cells. IL-7 may induce maturation of NK cell precursors, and may regulate proliferation of T cells. However, even though the composition does not include IL-7, IL-21, or a combination thereof, it may promote proliferation or activation of NK cells.

A concentration of IL-7 may be about 0.05 ng/ml to about 500 ng/ml, about 0.10 ng/ml to about 250 ng/ml, about 0.25 ng/ml to about 100 ng/ml, about 0.5 ng/ml to about 50 ng/ml, about 1.0 ng/ml to about 25 ng/ml, about 2.5 ng/ml to about 10 ng/ml, and a concentration of IL-7 may be about 0.05 ng/ml to about 500 ng/ml, about 0.10 ng/ml to about 250 ng/ml, about 0.25 ng/ml to about 100 ng/ml, about 0.50 ng/ml to about 50 ng/ml, about 2.5 ng/ml to about 10 ng/ml.

The medium refers to a material capable of supporting growth and survival of cells in vitro. The medium is not particularly limited, as long as it may be used in cell culture, and the medium may include, for example, one or more selected from the group consisting of Dulbecco's Modified Eagle's Medium (DMEM), Minimal Essential Medium (MEM), Basal Medium Eagle (BME), RPMI 1640, F-10, F-12, DMEM/F12, Minimal Essential Medium-α (MEM-α), Glasgow's Minimal Essential Medium (G-MEM), Iscove's Modified Dulbecco's Medium (IMDM), MacCoy's 5A medium, AmnioMax complete medium, AminoMax II complete medium, Endothelial Basal Medium (EBM) medium, and Chang's Medium.

The NK cells may have surface antigen characteristics of $CD3^-$ and $CD56^+$.

The culture may be for proliferation or activation of the NK cells. The proliferation of the NK cells means an increase in the number of cells, and may be used interchangeably with growth. The activation of the NK cells means that the above-described NK cells perform their functions, and may have surface antigen characteristics of $CD226^+$, $CD69^+$, $CD14^-$, $CD19^-$, $CD16^+$, or a combination thereof.

The surface antigen characteristics have the same meaning as immunological characteristics, and may be identified by observing cell surface markers (e.g., staining of cells with tissue-specific or cell-marker specific antibody) using a technique such as flow cytometry or immunocytochemistry, or by observing cell surface marker using an optical microscope or a confocal microscope, or by measuring changes in gene expression patterns using a technique known in the art, such as polymerase chain reaction (PCR) or gene expressing profiling.

The "positive or +" may mean that, with regard to a cell marker, the marker is present in a large quantity or at a high concentration, as compared with that of other reference cells. A marker exists inside a cell or on the surface of the cell, and therefore, when the marker may be used to distinguish the cell from one or more other types of cells, the cell may be positive for the marker. The positive may also mean that the cell has the marker with a signal intensity higher than a background signal, for example, in an amount sufficient to be signal-detected by a cell measuring device. For example, when cells may be detectably labeled with a CD56-specific antibody, and signals from the antibody are detectably higher than those of a control (e.g., background), the cell may be represented by "positive for CD56" or "$CD56^+$". The "negative or −" may mean that even though a specific cell surface marker-specific antibody is used, it is not detectable, as compared with a background. For example, cells may not be detectably labeled with a CD3-specific antibody. The cell may be represented by "negative for CD3" or "$CD3^-$".

Another aspect provides a method of culturing NK cells, the method including culturing NK cells in a medium including a composition for culturing NK cells, the composition including IL-15, IL-18, and IL-27.

The culturing method may be a method of proliferating NK cells in large quantities or a method of activating NK cells.

The method may further include, before culturing, obtaining peripheral blood mononuclear cells (PBMCs) from peripheral blood; and isolating NK cells from the obtained PBMCs.

The above process may further include removing cells having a surface antigen characteristic of $CD3^+$.

A method of isolating blood, a method of isolating PBMCs therefrom, a method of isolating NK cells therefrom, and a method of isolating or removing cells having specific surface antigen characteristics may be performed by a known method of using specific antibodies, etc.

According to the method, even when NK cells are cultured for a long time or sub-cultured several times, NK cells have excellent proliferative capacity, as compared with groups cultured with other cytokines, and therefore, NK cells may be obtained in large quantities.

According to the method, NK cells cultured by adding the composition may have increased interferon-gamma (IFN-gamma) secretion, as compared with groups cultured with other cytokines. Further, NK cells cultured by adding the composition may have increased cytotoxicity against cancer cells and may promote apoptosis of cancer cells, as compared with groups cultured with other cytokines.

The culture may be performed for about 7 days to about 2 days, about 7 days to about 30 days, about 14 days to about 30 days, about 15 days to about 27 days, about 16 days to about 26 days, about 17 days to about 25 days, about 18 days to about 24 days, about 19 days to about 23 days, or about 20 days to about 22 days.

Still another aspect provides NK cells prepared by the method of culturing NK cells.

Still another aspect provides a composition for preventing or treating cancer, the composition including NK cells prepared by the method of culturing NK cells.

Still another aspect provides use of the NK cells prepared by the method of culturing NK cells in preparing a pharmaceutical composition or formulation for preventing or treating cancer.

Still another aspect provides use of the NK cells prepared by the method of culturing NK cells in preparing a medical product for preventing or treating a disease, for example, cancer. The cancer may be solid cancer, lung cancer, liver cancer, breast cancer, uterine cancer, blood cancer, etc., but is not limited thereto. In cancer patients, the NK cells are reported to be closely related with development of diseases, such as lung cancer (Carrega P, et al., Cancer, 112, 863-875, 2008), liver cancer (Jinushi M, et al., J Hepatol., 43, 1013-1020, 2005), breast cancer (Bauernhofer T, et al., Eur J Immunol., 33, 119-124, 2003.), uterine cancer (Mocchegiani E., et al., Br j Cancer., 79, 244-250, 1999), blood cancer (Tajima F., et al, Lekemia, 10, 478-482, 1996), etc.

The composition may include a pharmaceutically acceptable carrier. In the composition, the "pharmaceutically acceptable carrier" refers to a material, generally, an inert material used in combination with an active ingredient to aid application of the active ingredient. The carrier may be an excipient, a disintegrant, a binder, a lubricant, a diluent, or a combination thereof. The excipient may be microcrystalline cellulose, lactose, low-substituted hydroxycellulose, or a combination thereof. The disintegrant may be sodium starch glycolate, anhydrous dibasic potassium phosphate, or a combination thereof. The binder may be polyvinylpyrrolidone, low-substituted hydroxypropyl cellulose, hydroxypropyl cellulose, or a combination thereof. The lubricant may be magnesium stearate, silicon dioxide, talc, or a combination thereof.

Still another aspect provides a method of treating cancer, the method including administering, to an individual, a therapeutically or pharmaceutically effective amount of the NK cells prepared by the method of culturing NK cells.

The term "administering" refers to introduction of a predetermined substance into an individual in any appropriate manner, and with regard to the administration route, the substance may be administered through any general route as long as it may reach a target tissue. The administration route may be intraperitoneal administration, intravenous administration, intramuscular administration, subcutaneous administration, intradermal administration, oral administration, topical administration, intranasal administration, intrapulmonary administration, or rectal administration, but is not limited thereto. In addition, administration may be performed by any apparatus capable of moving to a target cell. An administration dose may be appropriately selected according to the type of cancer, the administration route, a patient's age and gender, and severity of a disease, but for an adult, it may be administered at a dose of about $1 \times 10^6$ to about $1 \times 10^{11}$ cells on average.

The "therapeutically effective amount" means an amount sufficient to exhibit a therapeutic effect when administered to an individual or a cell in need of treatment. The "treatment" means treating a disease or medical condition in an individual, for example, a mammal, including a human, and the treatment includes: (a) prevention of generation of a disease or medical symptoms, i.e., preventive treatment of a patient; (b) relief of a disease or medical symptoms, i.e., removal or recovery of a disease or medical symptoms in a patient; (c) suppression of a disease or medical symptoms, i.e., slowing or stopping progression of a disease or medical symptoms in an individual; or (d) alleviation of a disease or medical symptoms in an individual.

Advantageous Effects of Disclosure

According to an aspect, in culturing NK cells from peripheral blood mononuclear cells, when NK cells are cultured in a medium including a composition for culturing NK cells, the composition including IL-15, IL-18, and IL-27, the NK cells may proliferate in large quantities and activation of NK cells may be promoted. Therefore, when the NK cells are used, cancer cell apoptosis or cancer cell-killing ability may be promoted, and therefore, the NK cells may be used as an effective adoptive immune cell therapy product in cancer prevention or treatment.

BRIEF DESCRIPTION OF DRAWINGS

FIG. 2B shows results of analyzing distributions of CD3$^-$ CD56$^+$ NK cells immediately (D0) after isolating PMBCs and NK cells from healthy normal individuals and 21 days (D21) after culturing the PMBCs and NK cells;

FIG. 4 shows results of examining effects of the composition for culturing NK cells of the present disclosure on NK cell activity;

FIG. 5B shows a graph showing the number and proliferation of NK cells as a result of culturing using 6-well plates for 0-5 days, culturing using T25 flasks for 5-12 days, and then culturing for 21 days after transferring to T75 flasks on day 21;

FIG. 6B shows graphs showing a growth curve and proliferation of NK cells when cultured using a mixed culture medium of cytokines IL-15, IL-18, and IL-27 and ITS;

MODE OF DISCLOSURE

Figure 1:
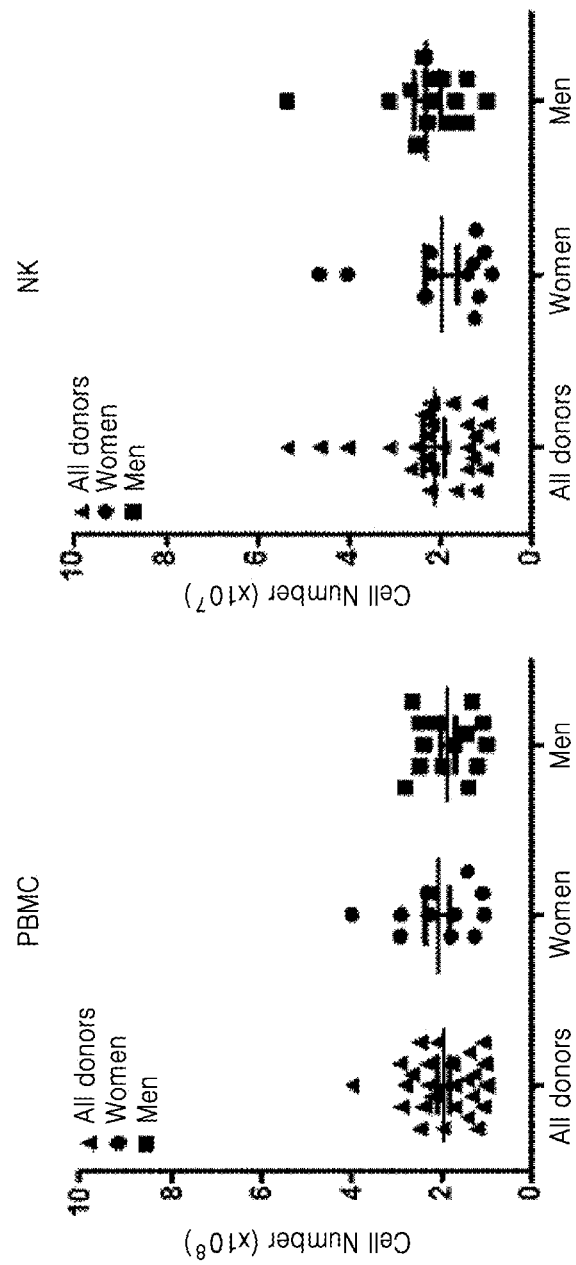
FIG. 1 shows results of counting the numbers of PBMCs and NK cells isolated from healthy normal individuals.

Hereinafter, the present disclosure will be described in more detail with reference to exemplary embodiments. However, these exemplary embodiments are only for illustrating the present disclosure, and the scope of the present disclosure is not limited to these exemplary embodiments.

Example 1: Isolation of Natural Killer (NK) Cells and Examination of Proliferative Capacity of NK Cells, Activity of NK Cells, and Cytotoxicity of NK Cells Against Cancer Cells, After Culturing NK Cells Using Composition for Culturing NK Cells 1. Isolation of NK cells and Culturing of NK cells using Composition for Culturing NK Cells (1.1) Selection of research subjects, Isolation of blood and PBMCs, and Isolation of NK cells Healthy males and females aged 20 to 65 years were subjects who agreed to blood collection for this study, and subjects eligible to participate in this study were selected based on health questionnaire, body weight, and vital signs. Subjects eligible to participate in the study were selected by the following criteria.

1) Those who do not have the following exclusions through health questionnaire

Those with a history of cardiovascular diseases such as hypertension, etc., kidney disease, diabetes, and cancer Those who refuse blood transfusion for religious reasons, etc.

Pregnant women

2) Males having body weight of 50 kg or more and females having body weight of 45 kg or more 3) Those who satisfy the following vital signs Blood pressure (mmHg): systolic pressure of 90 to 179 and diastolic pressure of less than 100

Body temperature (° C.): 37.5° C. or less

Pulse (beats/min): 50 to 100

On the day of visit, a total of 100 ml of blood was collected in a tube containing heparin once from those selected as research subjects, respectively.

From the collected blood, peripheral blood mononuclear cells (PBMCs) were isolated using Ficoll-Paque (GE Healthcare, 17-1440-02) by the following method. The collected whole blood was diluted 1:1 with phosphate buffered saline (PBS) (pH 7.4, Thermo Fisher Scientific), and the diluted blood was carefully added to the top of Ficoll. Subsequently, centrifugation was performed at 2500 rpm and 25° C. for 22 minutes to isolate PBMCs. The isolated PBMCs were washed with PBS. Thereafter, PBMCs without any treatment were stored before isolation of NK cells. Further, plasma obtained during the isolation process was also collected and stored.

From the isolated PBMCs, NK cells were isolated using an NK cell isolation kit (Miltenyi Biotec, 130-092-657) and $CD3^+$ magnetic beads (Miltenyi Biotec) by the following method, and $CD3^+$ cells were removed. MACS running buffer (PBS, 2 mM EDTA, 0.5% BSA) was added to the isolated PBMCs in a volume of 40 μl per $1 \times 10^7$ cells to suspend PBMC cell pellets, and then $CD3^+$ magnetic beads were added in a volume of 20 μl per $1 \times 10^7$ cells and allowed to react at 4° C. for 10 min. Subsequently, the cells were washed with MACS buffer, and then $CD3^-CD56^+$ NK cells were recovered using a MACS cell separator (Miltenyi Biotec).

FIG. 1 and Table 1 show results of counting the numbers of PBMCs and NK cells isolated from healthy normal individuals. FIG. 1 shows results of counting the number of PBMCs isolated from healthy normal individuals and the number of NK cells isolated from healthy normal individuals. As shown in FIG. 1 and Table 1, distribution of the $CD3^-CD56^+$ NK cells in PBMCs in the blood was about 8% to about 20% on average. There was no difference according to gender, and there was no statistically significant increase or decrease in NK cells according to age.

TABLE 1

| Gender | Age (years) | Number of healthy normal individuals | Average (Mean ± SD) | |
|---|---|---|---|---|
| | | | $PBMC(\times 10^8)$ | $NK(\times 10^7)$ |
| Female | 20-29 | 5 | 2.564 ± 0.952 | 2.526 ± 1.259 |
| | 30-39 | 5 | 1.634 ± 0.461 | 1.220 ± 0.139 |
| | 40 | 2 | 1.952 ± 1.294 | 2.455 ± 0.955 |
| | Total | 12 | | |
| Male | 20-29 | 2 | 2.385 ± 0.587 | 2.425 ± 0.955 |
| | 30-39 | 9 | 1.965 ± 0.579 | 2.294 ± 1.264 |
| | 40-49 | 3 | 1.237 ± 0.220 | 2.100 ± 0.383 |
| | Total | 14 | | |

Subsequently, whether NK cells in the isolated PBMCs and the collected NK cells had $CD3^-CD56^+$ characteristics was examined by fluorescence activated cell sorting (FACS, BD FACSCalibur).

Figure 2A:
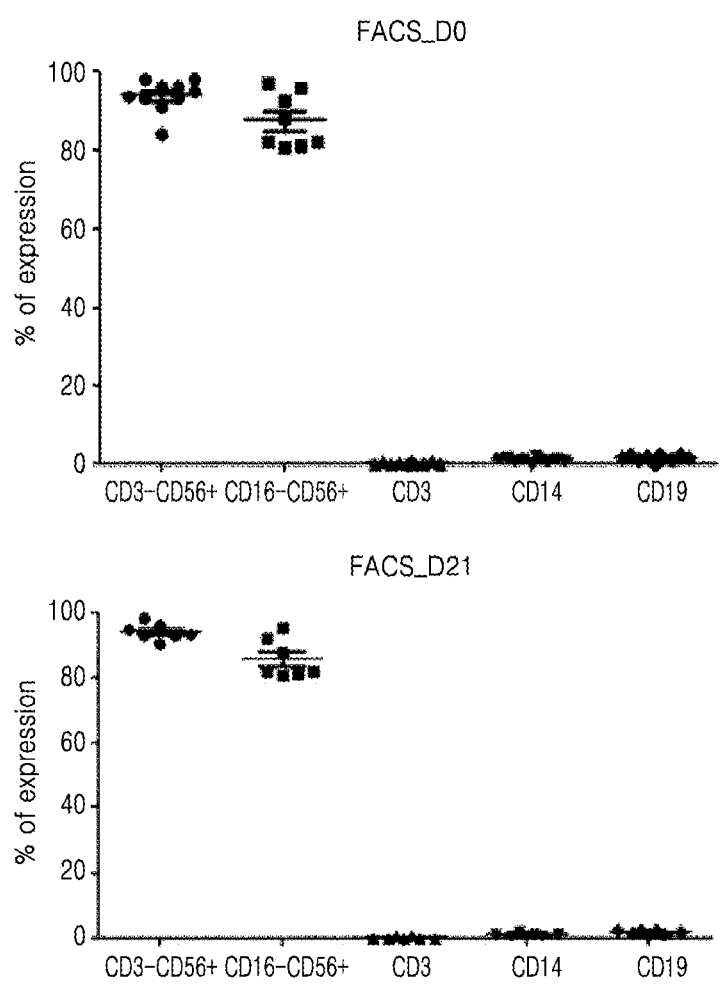
FIG. 2A shows FACS results of analyzing phenotypes of NK cells immediately (D0) after isolating the NK cells from PBMCs isolated from healthy normal individuals and 21 days (D21) after culturing the NK cells.

FIG. 2 shows FACS results of analyzing phenotypes of NK cells in PBMCs isolated from healthy normal individuals and the collected NK cells. FIG. 2A shows the results of analyzing phenotypes of NK cells immediately (D0) after isolating the NK cells and 21 days (D21) after culturing the NK cells. FIG. 2B shows results of analyzing distributions of $CD3^-CD56^+$ NK cells immediately (D0) after isolating PMBCs and NK cells and 21 days (D21) after culturing the PMBCs and NK cells.

Referring to FIG. 2, NK cells ($CD3^-CD56^+$) collected from healthy normal individuals (#8) had purity of 95% or more, and distributions of T cells, B cells, and monocytes were about 1% to about 2%. NK cells (D21) after culture for 21 days had purity of 98% or more.

(1.2) Culture of NK Cells Using Composition for Culturing NK Cells

NK cells obtained in (1) were added at a density of $1 \times 10^5$ cells/ml in each well of a 12- or 24-well tissue culture plate, and CellGro® serum-free medium (CellGenix, USA), 10% human serum (Sigma Aldrich, USA), 10,000 U/mL penicillin/streptomycin (Pen/Strep) (Gibco/Life Technologies, Carlsbad, Calif.), cytokine (IL-15, IL-27, 1-100 ng/ml; Peperotech, Inc. NJ, USA; IL-18, 1-100 ng/ml; R&D Systems, Inc., MN, USA), and ITS (Insulin-Transferrin-Selenium-G Supplement 100×, Gibco™) were added thereto, followed by culturing in an incubator at 37° C. and 5% $CO_2$ for 21 days.

In detail, 4 sets of cytokine combination treatment groups including a combination treatment group 1-1: IL-7 (5 ng/ml), IL-15 (10 ng/ml), IL-18 (25 ng/ml), IL-21 (5 ng/ml), and IL-27 (20 ng/ml), a combination treatment group 1-2: IL-15 (10 ng/ml), IL-18 (25 ng/ml), IL-21 (5 ng/ml), and IL-27 (20 ng/ml), a combination treatment group 1-3: IL-15 (10 ng/ml), IL-18 (25 ng/ml), and IL-27 (20 ng/ml), and a combination treatment group 1-4: IL-15 (10 ng/ml) and IL-18 (25 ng/ml) were mixed in a fresh medium, respectively, and then, once every 2 to 3 days, which is the time to replace the medium, the medium was added to the NK cells during culture, and cultured. Compositions of the media are the same as described above, except for cytokines.

Figure 2C:
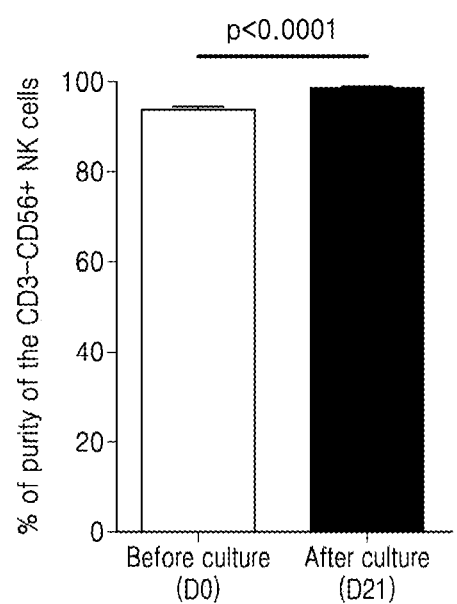
FIG. 2C shows results of calculating the purity of NK cells immediately (D0) after isolating the NK cells from PBMCs isolated from healthy normal individuals and 21 days (D21) after culturing the NK cells.

FIG. 2C shows results of analyzing the purity of NK cells immediately (D0) after isolating the NK cells and 21 days (D21) after culturing the NK cells. According to FIG. 2C, NK cells collected from the healthy normal individuals (#8) were found to have the purity of about 95% or more, even after cultured by adding the composition for culturing NK cells of the combination treatment group 1-3.

2. Examination of Proliferative Capacity of NK Cells and Activity of NK Cells After Cultured by Adding Composition for Culturing NK Cells (2.1) Examination of Proliferative Capacity of NK Cells After Cultured by Adding Composition for Culturing NK Cells The number NK cells proliferated during culture as in (1.2) was increased, starting from $1 \times 10^5$ cells/ml to $1 \times 10^6$ cells/ml of NK cells in a 6-well tissue culture plate to a large amount in T25, T75, and BAG (NIPRO cell culture bags, A-1000NL, A-350NL, Funakoshi Co., Ltd.) at intervals of 2 days to 3 days. Viability was determined using a hemocytometer after staining the propagated NK cells with a trypan blue staining agent (Thermo Fisher Scientific, USA).

Figure 3A:
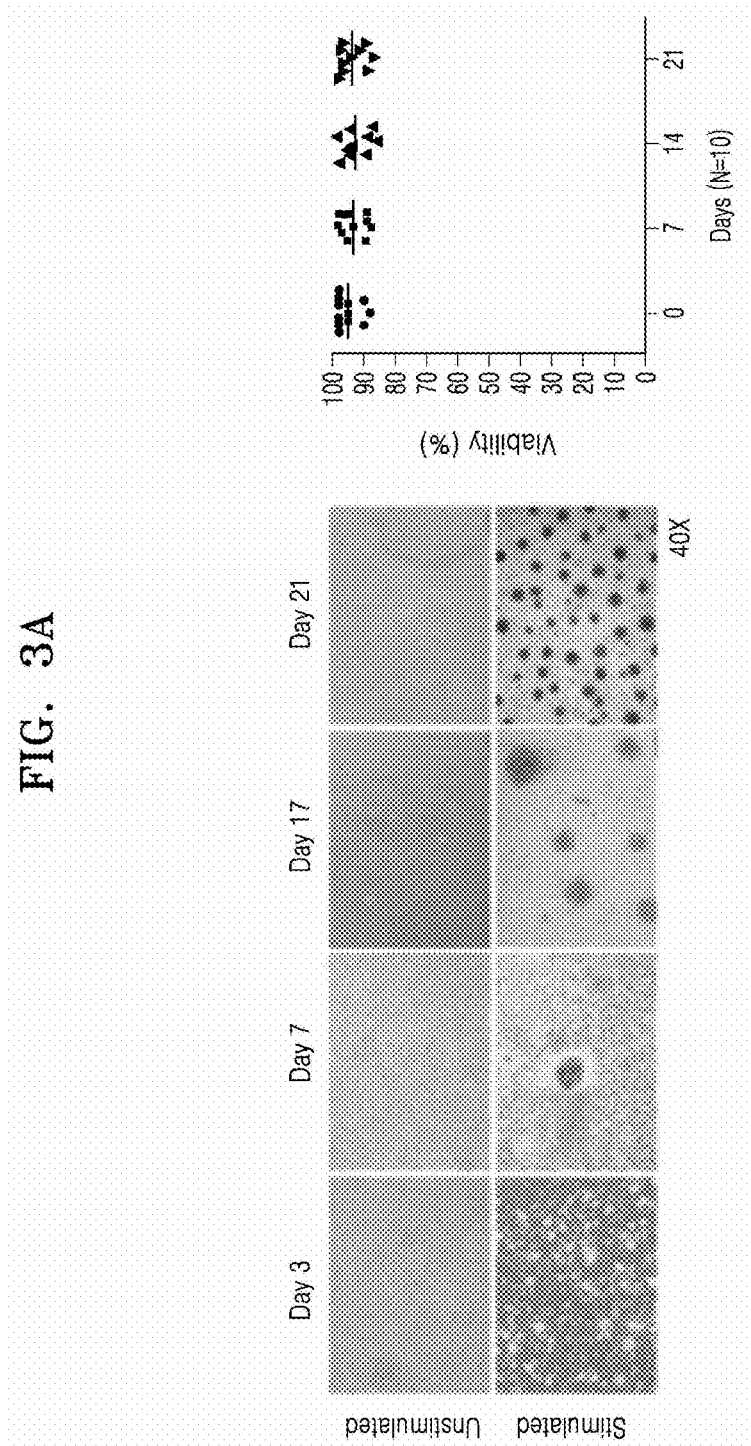
FIG. 3A shows photographs showing results of culturing NK cells for 3 days (Day 3), 7 days (Day 7), 17 days (Day 17), and 21 days (Day 21) in the composition for culturing NK cells of the present disclosure.
Figure 3B:
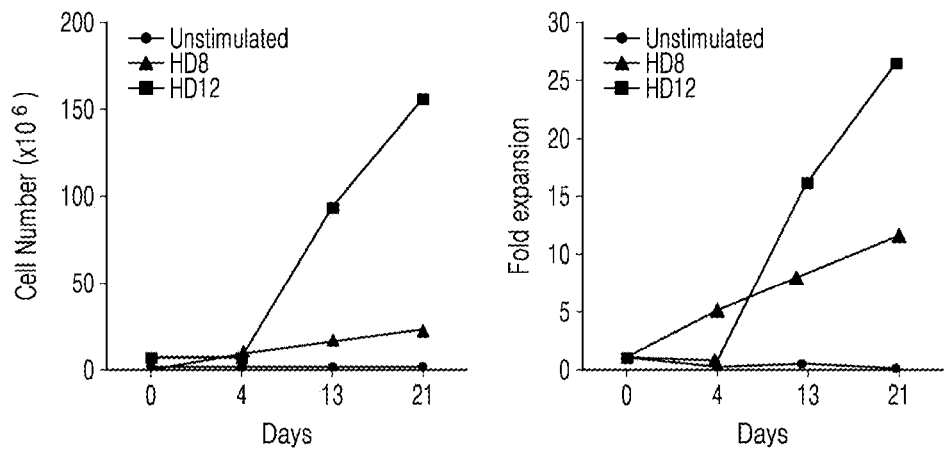
FIG. 3B shows graphs showing the numbers of NK cells cultured for 3 days (Day 3), 7 days (Day 7), 17 days (Day 17), and 21 days (Day 21) in the composition for culturing NK cells of the present disclosure.
Figure 3C:
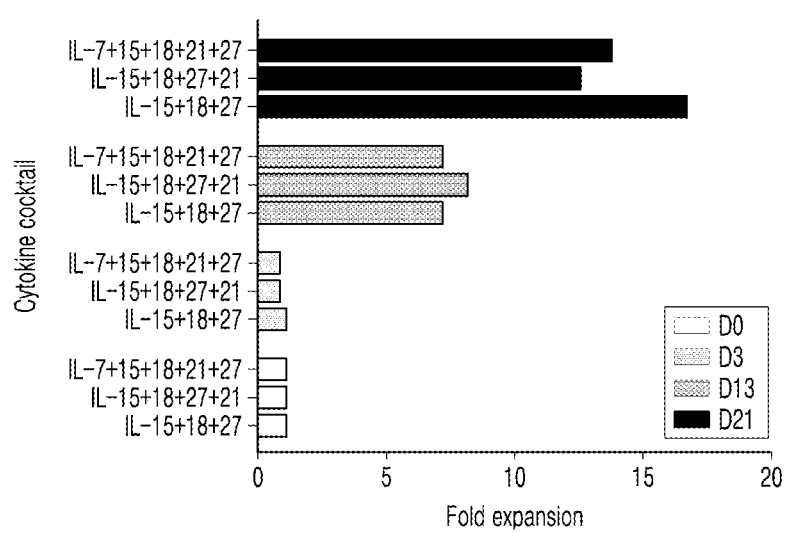
FIG. 3C shows a graph showing proliferation of NK cells on day 0 (D0), day 3 (D3), day 13 (D13) and day 21 (D21) according to cytokine cocktails.

FIG. 3 shows results of examining the effect of the composition for culturing NK cells of the present disclosure on proliferation and viability of NK cells. FIG. 3A shows photographs showing results of culturing NK cells for 3 days (Day 3), 7 days (Day 7), 17 days (Day 17), and 21 days (Day 21) in the composition for culturing NK cells of the present disclosure. As shown in FIG. 3A, when NK cells were cultured (stimulated) by adding the combination treatment group 1-3 among the compositions for culturing NK cells of the present disclosure, primary NK cells grew continuously while forming clusters, and their cell viability was as high as about 85% to about 90% on average for 21-day culture. FIG. 3B shows graphs showing the numbers of NK cells. As shown in FIG. 3B, the number of the NK cells of healthy normal individuals (#12) showed about 26 times increase from about $6 \times 10^6$ cells to $1.58 \times 10^8$ cells, after cultured for 21 days by adding the combination treatment group 1-3, as compared with those before culture. Further, the number of the NK cells of healthy normal individuals (#2) showed about 40 times and about 53.3 times increase, after cultured by adding the combination treatment group 1-2 and the combination treatment group 1-3, respectively. FIG. 3C shows a graph showing proliferation of NK cells on day 0 (D0), day 3 (D3), day 13 (D13) and day 21 (D21) according to cytokine cocktails. As shown in FIG. 3C, the proliferation of NK cells showed the significantly increased number of cells, when cultured for 21 days by adding the combination treatment group 1-3. Small differences between normal individuals were observed.

(2.2) Examination of Activity of NK Cells After Cultured by Adding Composition for Culturing NK Cells During culture as in (1.2), differences in activity of NK cells and receptor expression were examined.

During culture of NK cells, NK cells were collected, and $1 \times 10^5$ NK cells were dispensed in a FACS tube (Falcon® 5 mL Round Bottom Polystyrene Test Tube). An antibody of a target gene was added to the FACS tube, and allowed to react for 30 min. Thereafter, washing was performed using FACS buffer, and surface antigen characteristics were analyzed using fluorescence-activated cell sorting (FACS, BD FACSCalibur™). FlowJo program was used for data analysis.

| Target gene | | Company | Cat. |
|---|---|---|---|
| CD3 | APC | BD | 555342 |
| CD3 | PE | Invitrogen | 12-0038-42 |

-continued

| Target gene | | Company | Cat. |
|---|---|---|---|
| CD56 | FITC | BD | 562794 |
| CD56 | PE | BD | 555516 |
| Activating receptor | | | |
| CD314/NKG2D | PE | Thermo | 12-5878-42 |
| CD335 | PE | BD | 557991 |
| CD336 | PE | BD | 558563 |
| CD337 | PE | BD | 558407 |
| CD226 (DNAM) | PE | BD | 559789 |
| Inhibitor receptor | | | |
| NKG2A | PE | R&D | FAB1059P |
| KIR2DL4 (CD158d) | PE | R&D | FAB2238P-100 |
| KIR2DL5A (CD158f1) | PE | Origene | AM26776RP-N |
| KIR2DL1/158a | FITC | BD | 556062 |
| KIL2DL2/3 158b | FITC | BD | 559784 |
| KIR3DL1 (CD158e1, NKB1) | FITC | BD | 555966 |
| KIR3DL2 | PE | R&D | FAB2878P-100 |
| KIR3DL3 (CD158z) | Alexa 647 | R&D | FAB8919R-025 |
| Surface marker | | | |
| CD14 | PE | BD | 555398 |
| CD19 | FITC | BD | 555412 |
| CD69 | PE | Invitrogen | MHCD6904/ 1701544A |
| CD96 | PE | BD | 562379 |
| CD16 | PE | Thermo | MHCD1604 |

FIG. 4 shows results of examining effects of the composition for culturing NK cells of the present disclosure on NK cell activity. Referring to FIG. 4, an expression level of CD226 which is one of activating receptors on NK cells was increased from about 12.3% to about 95.7%, after cultured by adding the combination treatment group 1-3 (D21), as compared with those before culture (D0). Further, an expression level of CD69 which is an activation index was increased from about 3.3% to about 91.4%, after cultured by adding the combination treatment group 1-3 (D21), as compared with those before culture (D0). It was found that a large quantity of NK cells may be induced and proliferated only by using a small number of cytokines without feeder cells.

(2.3) Examination of NK Cell Proliferation Effect of ITS Addition

It was examined whether NK cell proliferation effect may be increased by adding insulin-transferrin-selenium (ITS) during culture of NK cells. NK cells were cultured for 21 days in three different culture media, each containing IL-2; IL-15 and IL-18; or IL-15 and IL-18 and IL-27 with or without ITS (Insulin-Transferrin-Selenium-G Supplement 100×, Gibco™). The results of culture are shown in FIG. 5.

Figure 5A:
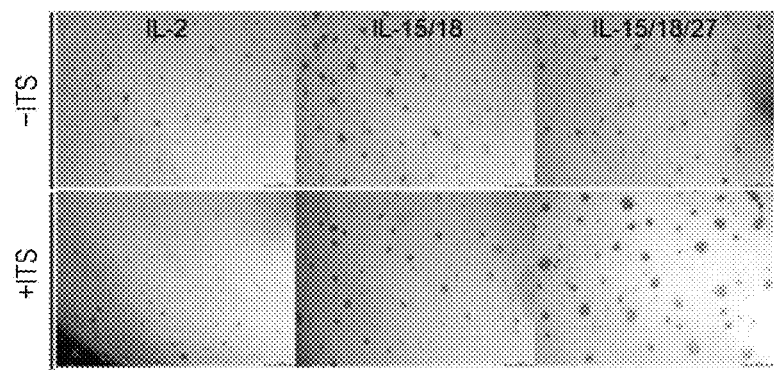
FIG. 5A shows photographs of NK cells cultured for 21 days in a culture medium containing IL-2; IL-15 and IL-18 (IL-15/18); or IL-15, IL-18, and IL-27 (IL-15/18/27), with ITS (+ITS) or without (−ITS)

FIG. 5A shows photographs of NK cells cultured for 21 days in a culture medium containing IL-2; IL-15 and IL-18 (IL-15/18); or IL-15, IL-18 and IL-27 (IL-15/18/27) with ITS (+ITS) or without (−ITS).

As shown in FIG. 5A, when ITS was added to the culture medium containing IL-2; IL-15 and IL-18; or IL-15 and IL-18 and IL-27, NK cells were more actively proliferated to form clusters, indicating a synergistic effect.

FIG. 5B shows a graph showing the number and proliferation of NK cells as a result of culturing using 6-well plates for 0-5 days, culturing using T25 flasks for 5-12 days, and then culturing for 21 days after transferring to T75 flasks on day 21.

As shown in FIG. 5B, in the NK cell proliferation, improvement in NK cell proliferation by ITS was observed. When treated with only IL-15/IL-18/IL-27, 13.76 times increase ($2.064 \times 10^7$) was observed, as compared with the initial. In contrast, when cultured with a mixture of IL-15/IL-18/IL-27 and ITS, 27.88 times increase ($4.1825 \times 10^7$) was observed.

Figure 5C:
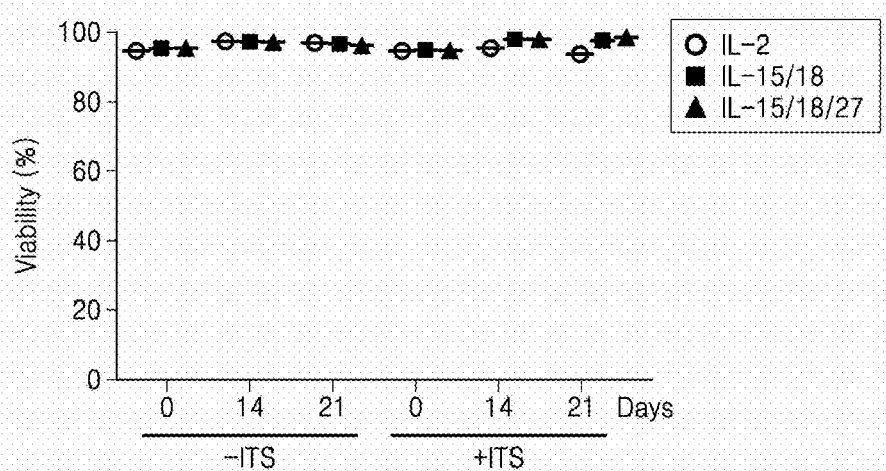
FIG. 5C shows results of examining cell viability of NK cells when the NK cells are cultured as in FIG. 5B.

FIG. 5C shows results of examining cell viability when the cells were cultured as above.

As shown in FIG. 5C, both two cells showed viability of 95% or more and cluster formation. Therefore, it was found that use of ITS does not influence cell viability.

Taken together, it was confirmed that addition of ITS may further improve the NK cell proliferation effect in the composition of culturing NK cells of the present disclosure.

(2.4) Examination of NK Cell Culture in Culture Bag

It was examined whether the method of culturing NK cells as confirmed above may be applied to mass-production of NK cells. In detail, NK cells obtained from the same subjects were activated using IL-15/18/27 early on days 0-7, and then ITS was added to the existing NK cell culture medium, followed by culture in a T25 plate. On days 7-12, the cells were transferred to several T25 plates, followed by culture. After 12-14 days of culture, the cells were transferred to a culture bag, followed by culture for 21 days.

FIG. 6 shows a photograph of NK cells cultured in the culture bag.

Figure 6A:
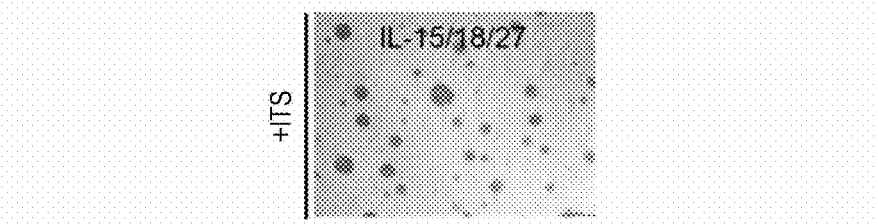
FIG. 6A shows a photograph showing morphology of NK cells when cultured using a mixed culture medium of cytokines IL-15, IL-18, and IL-27 and ITS.

FIG. 6A shows a photograph showing morphology of NK cells when cultured using a mixed culture medium of cytokines IL-15, IL-18, and IL-27 and ITS.

FIG. 6B shows graphs showing a growth curve and proliferation of NK cells when cultured using a mixed culture medium of cytokines IL-15, IL-18, and IL-27 and ITS.

As shown in FIGS. 6A and 6B, NK cells also formed clusters in the culture bag, as in the culture of using the plate. Further, cell growth was increased to $2.84 \times 10^8$, which was about 31.53 times, as compared with the initial number of NK cells, indicating continuous growth for 21 days.

Figure 6C:
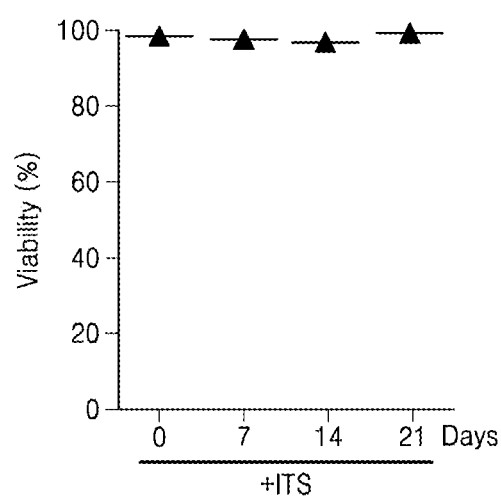
FIG. 6C shows a graph showing viability of NK cells when cultured using a mixed culture medium of cytokines IL-15, IL-18, and IL-27 and ITS.

FIG. 6C shows a graph showing viability of NK cells when cultured using a mixed culture medium of cytokines IL-15, IL-18, and IL-27 and ITS.

As shown in FIG. 6C, high cell variability of 98% or more was observed.

Therefore, when NK cells were cultured using the composition for culturing NK cells according to the present disclosure, the NK cell proliferation effect was observed not only in the plate but also in the culture bag, indicating that the composition may also be applied to mass-production.

3. Examination of Cytotoxicity of NK Cells Against Cancer Cells Using Composition for Culturing NK Cells (3.1) Examination of Cancer Cell Cytotoxicity of NK Cells Cultured by Adding Composition for Culturing NK Cells 1

(3.1.1) Cytotoxicity Assay

Cytotoxicity assay was performed for K562 cell (human chronic myelogenous leukemia cell line), which is generally used for measuring NK cell activity because of high sensitivity to NK cells, using a CytotTox-Glo™ cytotoxicity assay kit of Promega. This assay is a method of measuring an enzyme released as a result of cell membrane damage, in which enzymatic reaction of dead cells may be measured by examining a luminogenic peptide substrate (alanyl-alanyl-phenylalanyl-aminoluciferin, AAF-Glo Substrate).

K562 cells were dispensed at a density of $1 \times 10^4$ cells in each well of a 96-well plate coated with poly-D-lysine, and NK92 and NK cells for cytotoxicity assay were added thereto at an E:T ratio of 0:1, 1.25:1, 2.5:1, 5:1, or 10:1, and allowed to react for 4 hr. Thereafter, 50 μL of CytotTox-Glo™ cytotoxicity assay reagent was added and allowed to react at room temperature for 15 min, and then enzymatic activity of dead cells was measured using a luminometer. Subsequently, 50 μL of lysis buffer was added and allowed to react for 15 min, and then the total number of cells was examined. A percentage of the dead cells to the total number of cells was calculated to analyze cytotoxicity. At this time, the obtained data were analyzed using Microsoft Excel and GraphPad Prism 5.0.

Figure 7:
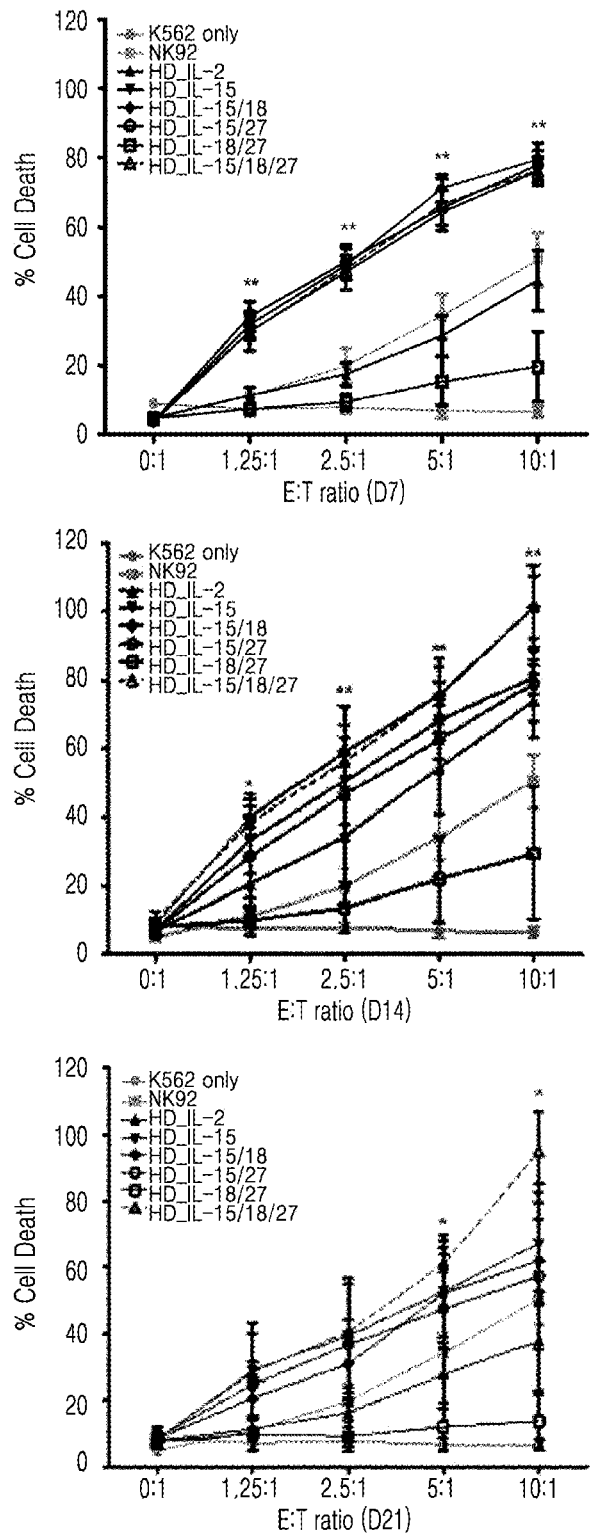
FIG. 7 shows results of examining cancer cell cytotoxicity of NK cells cultured by adding the composition for culturing NK cells of the present disclosure.

FIG. 7 shows results of examining cancer cell cytotoxicity of NK cells cultured by adding the composition for culturing NK cells of the present disclosure. Referring to FIG. 7, when cells were cultured using IL-2 alone, IL-15 alone, IL-15 and IL-18 (IL-15/18), IL-15 and IL-27 (IL-15/27), IL-18 and IL-27 (IL-18/27), or IL-15, IL-18 and IL-27 (IL-15/18/27), remarkably increased NK cytotoxicity was observed on day 7 (D7), day 14 (D14), and day 21 (D21) in NK cells cultured using a combination of two or more cytokines, as compared with those cultured using cytokine alone. In particular, when cultured using a combination of IL-15, IL-18, and IL-27, the highest cytotoxicity was maintained even during long-term (21 days) culture of NK cells. In a comparative experiment using an NK-92 cell line, the cytotoxicity assay value (RLU) of the NK cells was also 2 time or higher than that of NK-92. These results indicate that cancer cell cytotoxicity of NK cells stimulated with a combination of IL-15, IL-18, and IL-27 was further increased, as compared with those stimulated with IL-2 or IL-15 alone.

Additionally, cytotoxicity was also examined by measuring changes in expression of IFN-γ secreted by NK cells. In detail, during NK cell culture, 1 ml of NK cell culture medium was collected every 7 days. In the collected culture media, IFN-γ expression was measured using an enzyme-linked immunosorbent assay (ELISA, R&D, MN, USA), and results were analyzed using an ELISA Microplate Reader, and shown in FIG. 8.

Figure 8:
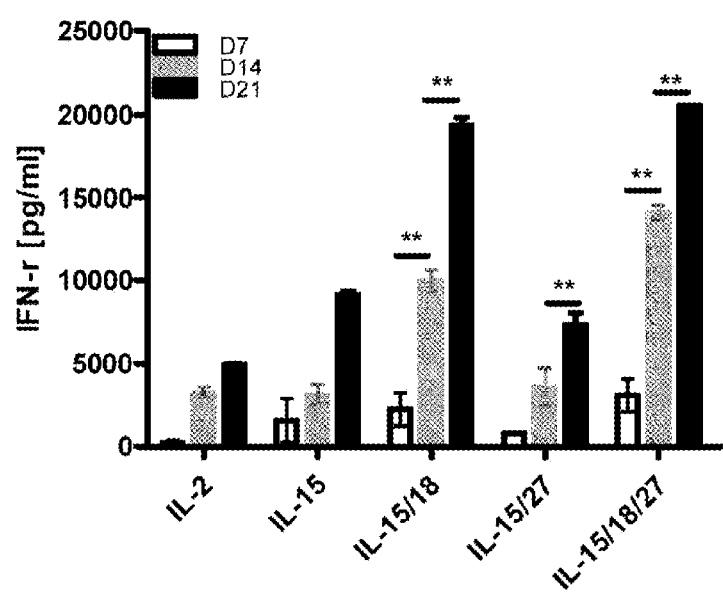
FIG. 8 shows a graph showing ELISA results of examining IFN-γ secreted from NK cells on day 7 (D7), day 14 (D14), and day 21 (D21) following culture.

FIG. 8 shows a graph showing ELISA results of examining IFN-γ secreted from NK cells on day 7 (D7), day 14 (D14), and day 21 (D21) following culture.

As shown in FIG. 8, when treated with IL-2 alone, IL-15 alone, IL-15 and IL-18 (IL-15/18), IL-15 and IL-27 (IL-15/27), or IL-15, IL-18, and IL-27 (IL-15/18/27), a high expression level of IFN-γ secreted by NK cells was observed in the IL-15/18/27-treated group, as compared with other cytokine-treated groups.

Therefore, stimulation of NK cells with cytokines effectively activated immune cells present in blood, leading to IFN-γ secretion. Further, since this result shows a significant relationship with the cytotoxicity result of NK cells, measurement of the IFN-γ secretion capacity of NK cells may represent cytotoxicity of NK cells.

(3.2.2) Calcein AM Assay

K562 cells stained with Calcein AM (Thermo Fisher Scientific) were dispensed at a density of $1 \times 10^5$ cells in each well of a 6-well plate coated with poly-D-lysine, and NK92 and NK cells for cytotoxicity assay were added thereto at an E:T ratio of 0:1, 1.25:1, 2.5:1, 5:1, or 10:1, and co-cultured for 21 days. Thereafter, a Calcein AM release assay was performed, and lysis of K562 cells by NK cells was observed under a fluorescence microscope (zeiss microscope).

Figure 9:
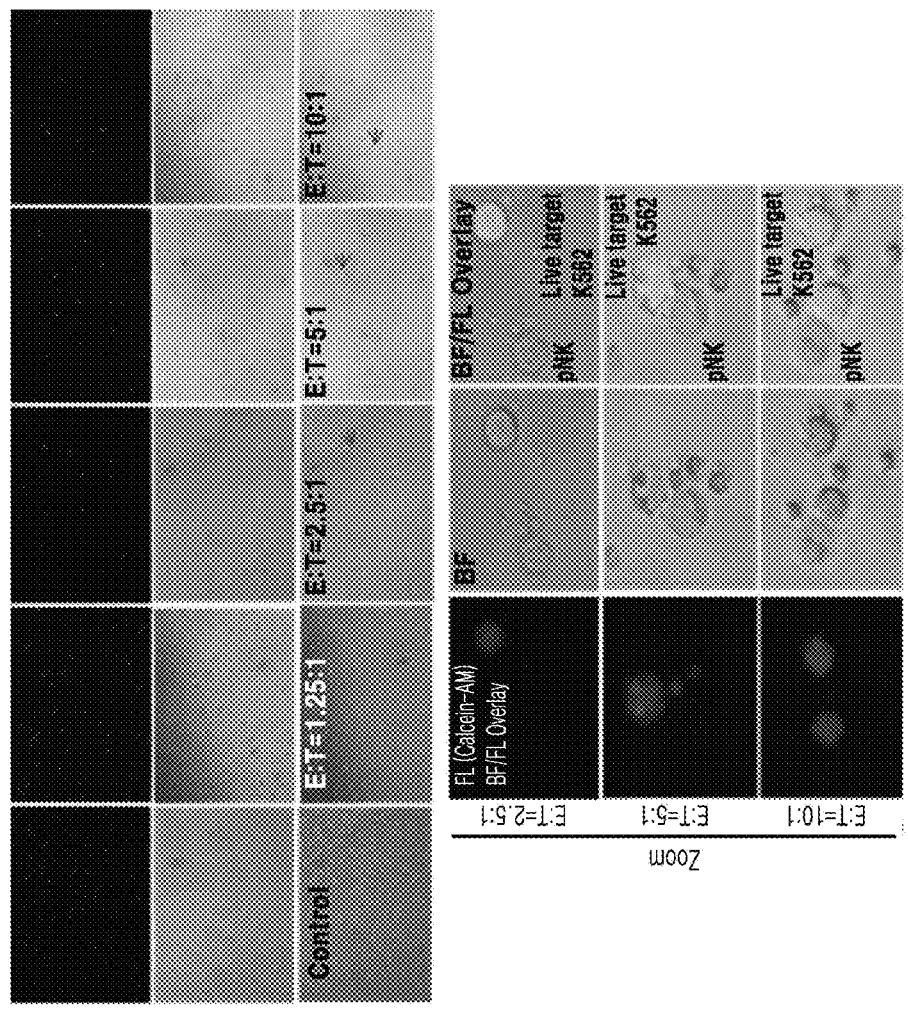
FIG. 9 shows results of examining cancer cell cytotoxicity of NK cells cultured by adding the composition for culturing NK cells of the present disclosure.

FIG. 9 shows results of examining cancer cell cytotoxicity of NK cells cultured by adding the composition for culturing NK cells of the present disclosure. The green-stained areas represent K562 cells. As shown in FIG. 9, as the ratio of NK cells (effectors) was higher, the number of live K562 cells was lower. This result suggests that apoptosis of K562 cell may be caused by interaction between NK cells and K562 cells.

(3.3) Examination of Cancer Cell Cytotoxicity of NK Cells Cultured by Adding Composition for Culturing NK Cells2.

(3.3.1) Caspase-3 Immunoblot

For in vitro cytotoxicity test of NK cells cultured by adding the composition for culturing NK cells of the present disclosure, ovarian cancer cells and NK cells were cultured, and then activity and expression levels of caspase-3 in the ovarian cancer cells were examined.

Ovarian cancer cells (A2780, SKOV3) were dispensed at a density of $1\times10^5$ cells in each well of a 6-well plate coated with poly-D-lysine, and on next day, $1\times10^5$ of NK92 and NK cells of the present disclosure for cytotoxicity assay were cultured with the ovarian cancer cells for 3 hr. Then, the culture medium and NK cells were removed, and only the remaining ovarian cancer cells were collected, followed by cell lysis using a lysis buffer. The cell lysate was heated at 95° C. for 10 min, and then proteins were isolated by centrifugation at 13,000 rpm for 20 min. The obtained proteins were separated using SDS-polyacrylamide gel electrophoresis (SDS-PAGE), and the separated proteins were transferred onto a polyvinylidene fluoride (PVDF) membrane (EMD Millipore, Billerica, Mass., USA). The PVDF membrane was incubated with 5% skim milk to block non-specific antibody binding. Subsequently, the PVDF membrane was reacted with a primary antibody, anti-caspase-3, and anti-actin at 4° C. overnight, respectively. On next day, primary antibody-bound PVDF membrane was reacted with a peroxidase-conjugated secondary antibody at room temperature for 1 hr. Protein bands were visualized and quantified using an enhanced chemiluminescence (ECL) kit system.

Figure 10:
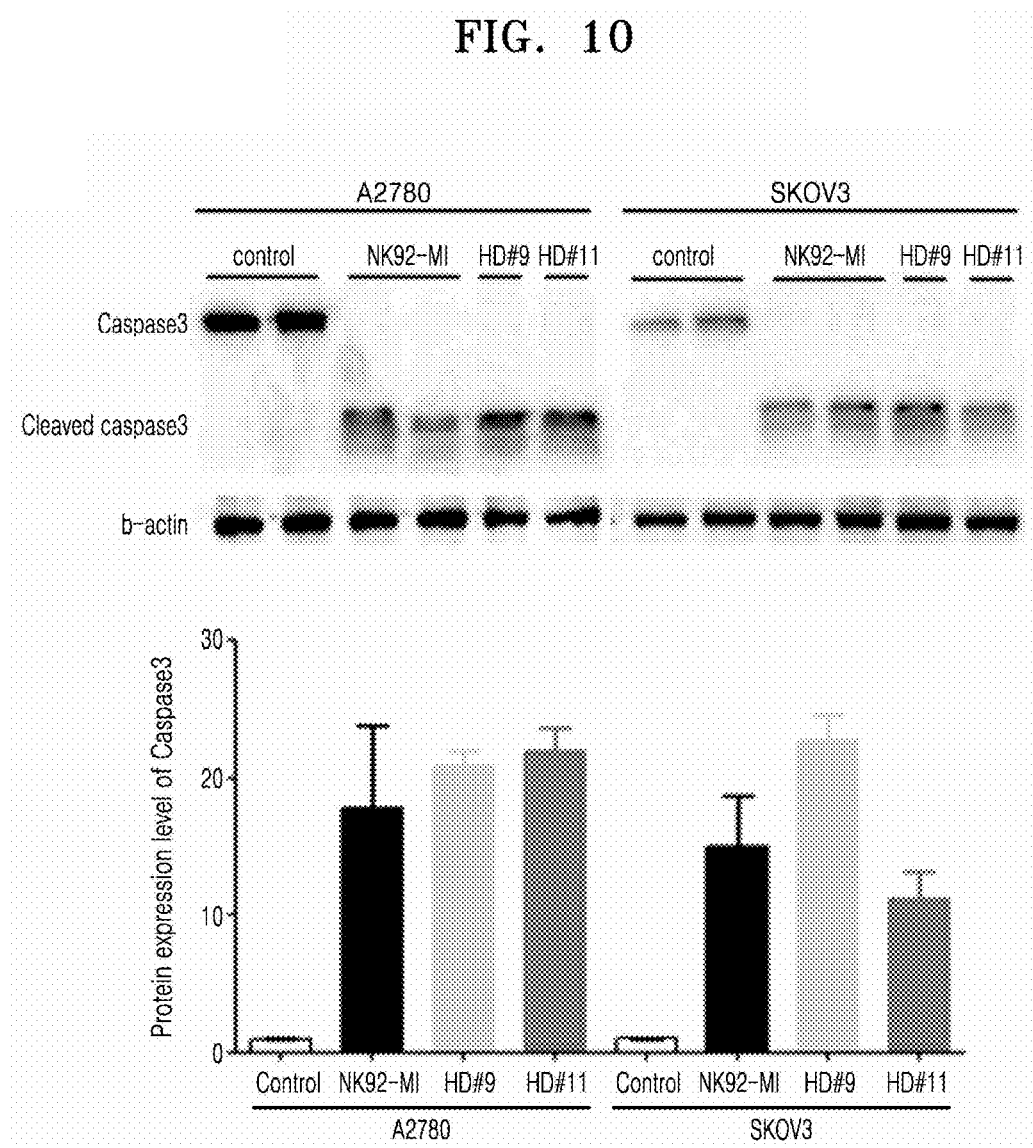
FIG. 10 shows results of examining activity, expression patterns, and expression levels of caspase-3 in cancer cells which were co-cultured with NK cells cultured by adding the composition for culturing NK cells of the present disclosure.

FIG. 10 shows results of examining activity, expression patterns, and expression levels of caspase-3 in cancer cells which were co-cultured with NK cells cultured by adding the composition for culturing NK cells of the present disclosure. With progression of apoptosis, a whole form of caspase-3 was decreased, and a cleaved form thereof was increased. As shown in FIG. 10, the cancer cells which were co-cultured with NK cells cultured by adding the composition for culturing NK cells of the present disclosure showed increased protein quantity of caspase-3 cleaved form, indicating a significant increase of cytotoxicity against cancer cells. Further, the expression level of caspase-3 cleaved form in cancer cells which were co-cultured with NK cells cultured by adding the composition for culturing NK cells of the present disclosure showed about 5% to about 10% increase, as compared with that of cancer cells co-cultured with NK92 cells.

(3.3.2) Caspase-3 Immunofluorescence Staining

Subsequently, apoptosis progression in cancer cells was examined.

Ovarian cancer cells (A2780, SKOV3) were dispensed on a chamber slide coated with poly-D-lysine, and on next day, the equal numbers of NK92 cells and NK cells of the present disclosure were cultured with the ovarian cancer cells for 3 hr, respectively. The culture medium and NK cells were removed, and the remaining ovarian cancer cells were subjected to immunofluorescence staining. As a primary antibody, anti-caspase3 and anti-actin were used, and as a secondary antibody, Alexa 488 goat anti-rabbit and Alexa 546 goat anti-mouse were used. Actin and DAPI were used as controls. After staining, the slide was mounted, and observed under a confocal laser-scanning microscope.

Figure 11:
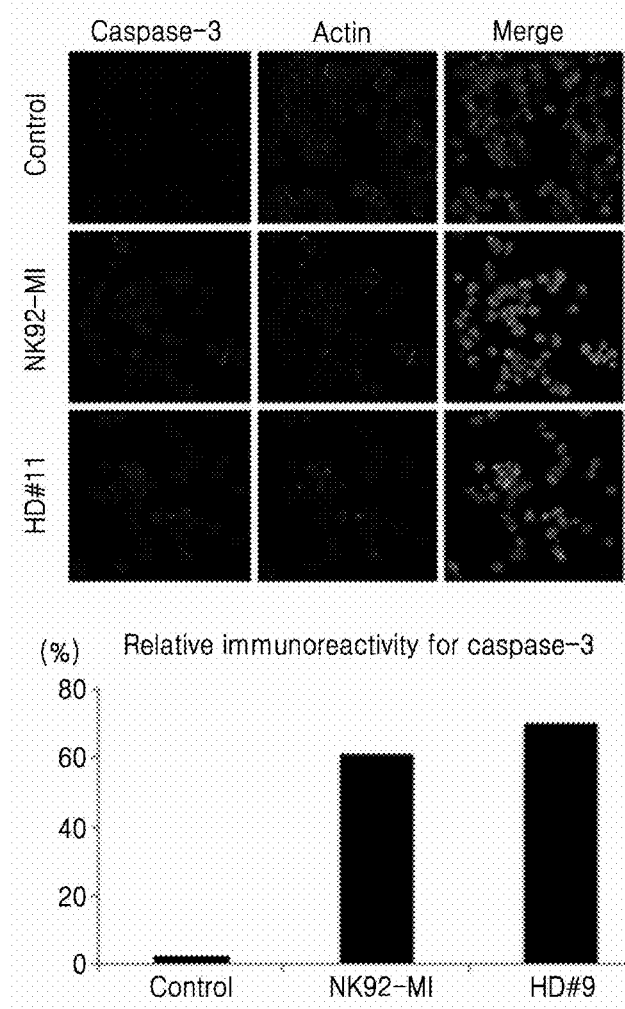
FIG. 11 shows images of expression levels and expression locations of caspase-3 in cancer cells which were co-cultured with NK cells cultured by adding the composition for culturing NK cells of the present disclosure.

FIG. 11 shows images of expression levels and expression locations of caspase-3 in cancer cells which were co-cultured with NK cells cultured by adding the composition for culturing NK cells of the present disclosure.

As shown in FIG. 11, the cancer cells which were co-cultured with NK cells cultured by adding the composition for culturing NK cells of the present disclosure showed about 50% or more increase in the caspase-3 activity, as compared with the control, and about 10% or more increase in the caspase-3 activity, as compared with cancer cells co-cultured with NK92 cells as another control.

The invention claimed is:

1. A method of culturing natural killer cells (NK cells), the method comprising culturing the NK cells in a composition for culturing NK cells, the composition comprising IL-15 in an amount of 5.0 ng/ml to 20 ng/ml, IL-18 in an amount of 0.25 ng/ml to 2500 ng/ml, IL-27 in an amount of 0.20 ng/ml to 2000 ng/ml, and insulin transferrin selenium (ITS).

2. The method of claim 1, wherein the cultured NK cells are CD226$^+$, CD69$^+$, C14$^-$, CD19$^-$, CD16$^-$, or a combination thereof.

* * * * *